United States Patent [19]

Kronman et al.

[11] 3,943,628
[45] Mar. 16, 1976

[54] SPOON EXCAVATOR FOR APPLYING CHEMICALLY ACTING TOOTH DECAY ATTACKING FLUID

[76] Inventors: Joseph H. Kronman, 51 Algonquin Road, Canton, Mass. 02021; Melvin Goldman, 8 Herbert Road, Worcester, Mass. 01602

[22] Filed: Mar. 19, 1974

[21] Appl. No.: 452,649

[52] U.S. Cl. ............................................. 32/40 R
[51] Int. Cl.² ......................................... A61C 3/00
[58] Field of Search .......... 128/239, 222; 32/58, 59, 32/40 R

[56] References Cited
UNITED STATES PATENTS

| | | | |
|---|---|---|---|
| 3,605,721 | 9/1971 | Hallac | 128/2 B |
| 3,732,869 | 5/1973 | Bronstein | 128/2 B |
| 3,807,048 | 1/1972 | Malmin | 32/40 R |

*Primary Examiner*—Robert Peshock
*Attorney, Agent, or Firm*—Cushman, Darby & Cushman

[57] ABSTRACT

A spoon excavator for administering a solution of N-monochloroglycine or other N-haloamine or like solution for effecting and facilitating dissolution of dental caries. The spoon excavator has a tubular shaft connected to a source of solution and a tip portion flattened and shaped to provide a generally spoon-like configuration for facilitating caries removal.

12 Claims, 4 Drawing Figures

SPOON EXCAVATOR FOR APPLYING CHEMICALLY ACTING TOOTH DECAY ATTACKING FLUID

BACKGROUND OF THE INVENTION

N-monochloroglycine solutions having a pH of 8–12 and other N-haloamine solutions have been recognized to have the capability of dissolving dental plaque and dental caries while not adversely affecting healthy dental structures. Some basic compositions having the above-mentioned capabilities are disclosed in our copending application Ser. No. 307,835 filed Nov. 20, 1972, which is a continuation-in-part of application Ser. No. 117,822, filed Feb. 22, 1971, now abandoned, and application Ser. No. 197,966, filed Nov. 11, 1971, now abandoned, although the present invention is not restricted to use with the liquids so described, but is utilizable with any chemically active decay attacking fluid. Suitable solutions include, but are not limited to, solutions of N-chloroglycine, N-bromoglycine, N-iodoglycine, N-chlorosarcosine, N-bromosarcosine, N-iodosarcosine, N-chloro alpha amino isobutyric acid, N-chlorotaurine, N-bromotaurine, N-iodo taurine, N-chloro ethanolamine, N-ethanolamine, N-ido-N-acetyl glycine, N-bromo, N-acetyl glycine, N-chloroalanine, N-chloro beta alanine, N-bromo beta alanine, N-chloroserine, N-bromoserine, N-iodoserine, N-chloro-N-phenylalanine, N-chloroisoleucine, N-chlorornorvaline, N-chloroleucine, N-bromoleucine, N-iodoleucine, N-chloroproline, N-bromo-proline, N-iodoproline, N-chloro hydroxyproline, N-chloro omega aminoundecanoic acid, N-chloroaspartic acid, N-bromoaspartic acid, N-chloroglutamic acid, N-iodoglutamic acid, N-chlorovaline, N-chlorotyrosine, N-bromotyrosine, N-iodotyrosine, N-chlorothreonine, N-chlorocysteine, N-chlorocystine, N-chloromethionine, N-bromomethionine, N-chlorotryptophane, N-chlorohistidine, N-chloroargenine, N-chloroglutamine, N-bromoglutamine, N-chlorolysine, N-chloro gamma aminobutyric acid, N-chloro alpha, epsilon diaminopimelic acid, N-chloro ornithine, N-chloro hydroxylysine, N-chloroanthranilic acid, N-chloro p-ami-nobenzoic acid, N-chlorosulfanic acid, N-chloro phenyl-sulfamic acid, N-chloro aminopropanesulfonic acid, N-aminomethanesulfonic acid, N-chloropropanolamine, N-chlorodiethanolamine, N-chloro-ethylene diamine tetra-acetic acid (in this compound the nitrogen atom apparently functions as a quaternary nitrogen).

One method of applying such solutions has been by spraying the liquid directly on the surface of the caries. Thus the instrument shown in Vit. U.S. Pat. No. 3,776,825, is very similar in size and shape to a conventional hypodermic needle, and since the tip is pointed and sharp, pressure must be light to prevent pain to the patient and to prevent possible digging into the caries with subsequent blockage of the egress of the solution. The entire disclosure of the Vit patent is hereby incorporated by reference. Removal of the caries has in the past been facilitated by utilization of a spoon excavator or a rotary burr after application of the liquid.

The device of the present invention effects application of chemically active decay attacking fluid, assists in obtaining proper access to the area to be treated, and facilitates removal of the caries both before, during, and after application of the solution while not interfering with liquid flow. A needle has its end flattened and shaped in the form of a spoon excavator, and the needle is hooked up to a source of supply for the solution. The spoon excavator tip can be used to lift areas of the carious material to provide better access to the caries by the liquid, some of the gross caries can be freed and lifted away by the tip, and flow of liquid can be stopped and the tip used as a conventional spoon excavator without the need to stop, place the handpiece and needle tip back in its holder, pick up the spoon excavator, and reverse the process to apply more solution. The device of the present invention thus takes full advantage of the properties of chemically active decay attacking fluids in eliminating caries from teeth for subsequent filling. The device of the present invention can be used to replace the hypodermic needle in the aforementioned Vit patent, and can be used for treating both humans and animals.

It is an object of the present invention to provide an improved means for applying chemically active decay attacking fluids to dental caries.

It is a further object of this invention to provide a means for providing better access of chemically active decay attacking fluid to caries.

It is a further object of the present invention to provide a means for assisting in removal of caries treated with chemically active decay attacking fluids, e.g. liquids.

It is a still further object of the present invention to provide an instrument that is specially adapted to both administer chemically active decay attacking fluid and perform as a spoon excavator.

These and other objects of the invention will become clear upon an inspection of the ensuing detailed description of the invention and the appended claims.

DETAILED DESCRIPTION OF THE INVENTION

Figure 1:
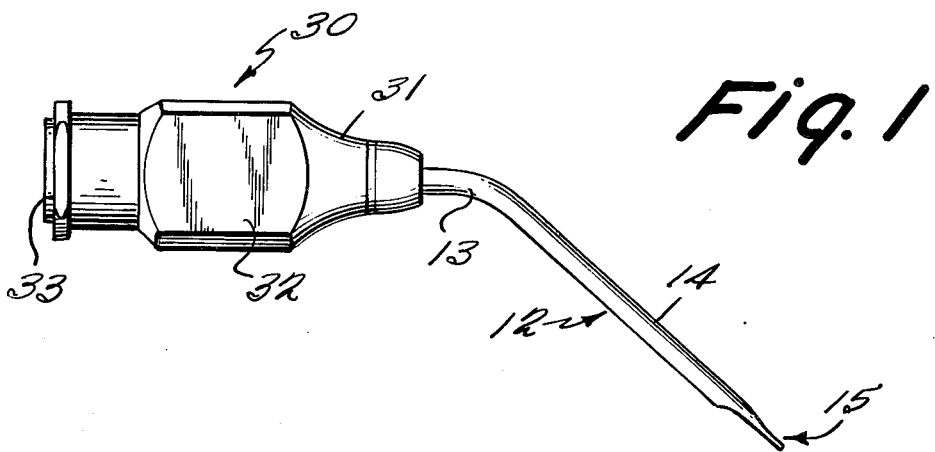
FIG. 1 is a side elevational view of the instrument according to the teachings of the present invention attached to a handpiece for connection to a source of supply of chemically active decay attacking fluid.

The instrument according to the teachings of the present invention is shown generally at 10 in FIG. 1. The instrument consists generally of a needle-like member 12 and a handpiece 30 for manipulation of the needle-like member and for connection to a source of supply of chemically active decay attacking fluid, e.g., a solution of an N-haloamine in a liquid. The tubular member 12 is preferably formed to be equivalent in size and diameter to the ordinary 20 gauge hypodermic needle, although many other sizes are suitable. The tubular portion 12 consists of a curved end portion 13 for connection to the handpiece 30, a shaft 14, and a working tip portion 15. Although the portion 13 is disclosed as bent to facilitate utilization of the device in a person's mouth, it could have another suitable contour.

Figure 2:
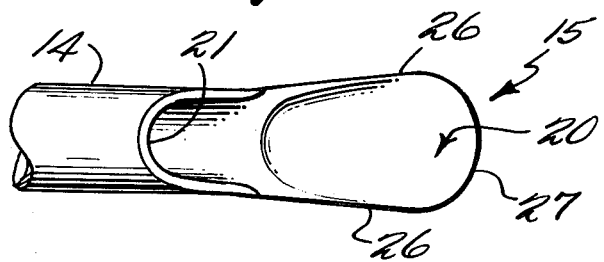
FIG. 2 is a top plan view of the tip of the instrument according to the teachings of the present invention.
Figure 3:
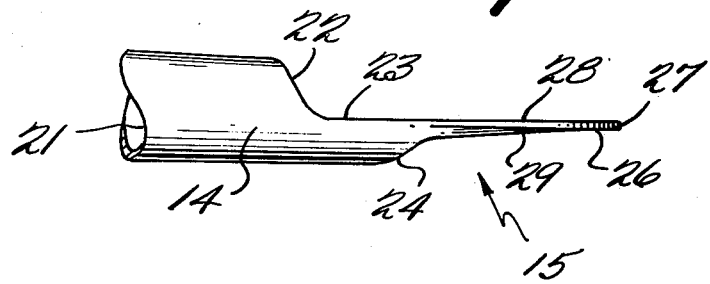
FIG. 3 is a side elevational view of the tip of the instrument according to the teachings of the present invention.
Figure 4:
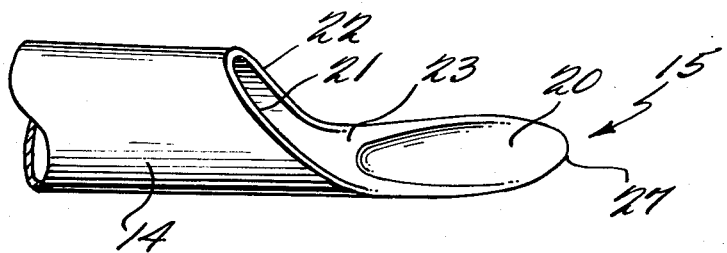
FIG. 4 is a perspective view of the tip of the instrument according to the teachings of the present invention.

The working tip portion 15 is shown in detail in FIGS. 2–4. The tip portion terminates in the flattened termination portion shown generally at 20, the portion 20 having a flat top surface 28, a recessed bottom surface 29, side surfaces 26 diverging outwardly from the contour of shaft 14, and then converging at rounded off surface 27 at the extreme end thereof. In being so shaped, the terminating portion 20 can be used to lift up relatively large areas of carious material to provide better access for the chemically active decay attacking liquid or other fluid, and can be used to remove caries during and after application of the fluid to hasten its effect, while not interfering in the least with free albeit still directed flow of the fluid from lumen 21 in shaft 14.

The transition from the shaft 14 to the terminating portion 20 is accomplished via surfaces 22–24. Generally beveled surface 22 leads from the contour of shaft 14 to flat portion 23. Top surface 28 of terminating portion 20 is an extension of flat portion 23. Curved surface 24 provides the transition from the bottom surface 29 of termination 20 to the contour of shaft 14. By forming the surfaces in such a manner, the top surface 27 of termination 20 generally bisects lumen 21 of shaft 14, and free albeit still directed flow of liquid from lumen 21 to the target area is provided.

The handpiece for manipulation of the needle-like member and for connection to the chemically active decay attacking fluid supply means is shown generally at 30 in FIG. 1. In FIG. 1, handpiece 30 is shown as having a portion 31 for connection to curved needle end portion 13, a middle portion 32 shaped to be easily grasped by a hand, and an end portion 33 for connecting to a hose leading to a liquid reservoir or pump. The means 30 is suitable for connection in place of the hypodermic needle in a system such as is depicted in the above-mentioned U.S. Pat. No. 3,776,825. Alternatively, a conventional Water Pic supply system could be utilized in place of means 30, or an ordinary syringe or like device. It is preferable to have a supply for administering the fluid under pressure, however, since the mechanical action of the fluid flow against the caries assists the chemical action of the fluid and the mechanical action of the tip 15 in removing the caries.

It will be apparent to one of ordinary skill in the art that many modifications of the present invention are possible. While the invention has been illustrated in an embodiment preferred for accomplishing the functions of assisting in providing access to carious material, applying liquid to the caries, and excavating caries while not interfering with liquid flow, other forms are possible including but not limited to variations in size, shape, and contour of the various parts. Thus, it is recognized that departures may be made from the illustrated most practical and preferred embodiments that are within the scope of the invention, which scope is not to be limited except by the following claims.

What is claimed is:

1. A dental instrument comprising
    a. a source of supply of chemically active decay attacking fluid, and
    b. means for administering said fluid from said source of supply to dental caries, assisting in providing access to said caries by said fluid, and excavating said caries while not interfering with flow of said fluid, said means including a tubular member for conducting fluid from said fluid supply having an open working end thereof formed as a spoon excavator, having side surfaces outwardly diverging from the contour of said tubular member, a generally curved terminating surface, a generally flat top surface, and a generally depressed bottom surface.

2. A dental instrument as recited in claim 1 wherein transition is provided between said top surface of said spoon excavator working end and said contour of said tubular member by a generally beveled portion and a generally flat portion of which said top surface of said spoon excavator working end is an extension, and wherein transition is provided between said bottom surface of said spoon excavator working end and said contour of said tubular member by a generally curved portion.

3. A dental instrument as recited in claim 1 wherein said top surface of said spoon excavator working end of said tubular member substantially bisects said tubular member, whereby free albeit still directed flow of fluid from said tubular member past said spoon excavator working end is allowed.

4. A dental instrument as recited in claim 1 wherein said instrument further comprises a handpiece for connection to said source of fluid supply and for facilitating manipulation of said administering, assisting, and excavating means, said handpiece connected to the open end of said tubular member remote from said open working spoon excavator end thereof.

5. A dental instrument as recited in claim 1 wherein said chemically active decay attacking fluid is a solution of N-monochloroglycine at a pH between 8 and 12.

6. A dental instrument as recited in claim 1 wherein said chemically active decay attacking fluid is an aqueous solution of N-monochloroglycine at a pH between 9 and 11.5.

7. A dental instrument as recited in claim 1 wherein said chemically active decay attacking fluid is a solution of N-monohaloamine having a pH between 8 and 12.

8. A dental instrument comprising a tubular member for administering chemically active decay attacking fluid to caries,
    said tubular member having an open end thereof formed as a spoon excavator for assisting in providing access to said caries by said fluid and for excavating said caries while not interfering with flow of fluid, said spoon excavator end having side surfaces outwardly diverging from the contour of said tubular member, a generally curved terminating surface, a generally flat top surface, and a generally depressed bottom surface,
    the other open end of said tubular member being adapted to be connected to a source of supply of said fluid.

9. A dental instrument as recited in claim 8 wherein said instrument further comprises a handpiece connected to said other end of said tubular member, said handpiece having an opening therethrough to provide communication between a source of supply of said fluid and said tubular member.

10. A dental instrument as recited in claim 9 wherein said tubular member is bent near the end thereof connected to said handpiece, whereby utilization of said instrument in a patient's mouth is facilitated.

11. A method of removing dental caries or plaque comprising the steps of
    inserting a tubular member having the working open end thereof formed as a spoon excavator into a patient's mouth, said spoon excavator working open end having side surfaces outwardly diverging from the contour of said tubular member, a generally curved terminating surface, a generally flat top surface, and a generally depressed bottom surface, using said member to assist in providing access of chemically active decay attacking fluid to said plaque or caries through said tubular member, and excavating said caries or plaque with said spoon excavator end of said tubular member.

12. A method as recited in claim 11 wherein said steps are repeated until said caries or plaque have been effectively removed.

* * * * *